United States Patent
Eriksson et al.

(10) Patent No.: US 10,953,010 B2
(45) Date of Patent: Mar. 23, 2021

(54) IMATINIB FOR USE IN THE TREATMENT OF STROKE

(71) Applicants: HAMRA INVEST AB, Bålsta (SE); BRAIN CONSULTANT NILS GUNNAR WAHLGREN AB, Bromma (SE)

(72) Inventors: Ulf Eriksson, Bålsta (SE); Nils Gunnar Wahlgren, Bromma (SE)

(73) Assignees: Hamra Invest AB, Bålsta (SE); Brain Consultant Nils Gunnar Wahlgren AB, Bromma (SE)

(*) Notice: Subject to any disclaimer, the term of this patent is extended or adjusted under 35 U.S.C. 154(b) by 0 days.

(21) Appl. No.: 16/080,529

(22) PCT Filed: Feb. 27, 2017

(86) PCT No.: PCT/SE2017/050183
§ 371 (c)(1),
(2) Date: Aug. 28, 2018

(87) PCT Pub. No.: WO2017/151043
PCT Pub. Date: Sep. 8, 2017

(65) Prior Publication Data
US 2019/0030030 A1    Jan. 31, 2019

(30) Foreign Application Priority Data
Feb. 29, 2016  (SE) ...................................... 1650260

(51) Int. Cl.
*A61K 31/506*   (2006.01)
*A61K 9/00*     (2006.01)
*A61P 9/10*     (2006.01)

(52) U.S. Cl.
CPC .......... *A61K 31/506* (2013.01); *A61K 9/0019* (2013.01); *A61K 9/0053* (2013.01); *A61P 9/10* (2018.01)

(58) Field of Classification Search
CPC .. A61K 31/506; A61K 9/0019; A61K 9/0053; A61P 9/10
See application file for complete search history.

(56) References Cited

U.S. PATENT DOCUMENTS

2009/0264438 A1   10/2009   Jegorov et al.
2010/0136094 A1    6/2010   Hyde et al.

FOREIGN PATENT DOCUMENTS

WO   2006/121941 A2   11/2006
WO   2007124308       11/2007

OTHER PUBLICATIONS

Diener et al. Treatment of acute ischaemic stroke with thrombolysis or thrombectomy in patients receiving anti-thrombotic treatment. Lancet Neurol. 2013; 12: 677-88.*

(Continued)

*Primary Examiner* — Anna Pagonakis
(74) *Attorney, Agent, or Firm* — Myers Bigel, P.A.

(57) ABSTRACT

Imatinib can be used in the treatment of stroke in a new dosage regime, where Imatinib is administered to the patient at a dose of 650 mg/day or higher for at least 3 consecutive days, and preferably administered in a starting dose of 1000 mg/day or higher on day 1, and at a dose in the interval of 650 mg/day to 1000 mg/day on the subsequent days. A method for the treatment of stroke, a pharmaceutical composition and a kit of parts is/are also disclosed.

18 Claims, 3 Drawing Sheets

(56) References Cited

OTHER PUBLICATIONS

Su et al. Activation of PDGF-CC by tissue plasminogen activator impairs blood-brain barrier integrity during ischemic stroke. Nature Medicine, vol. 14. No. 7, Jul. 2008.*
Toeh et al. Pharmacokinetics, tissue distribution and bioavailability of imatinib in mice after administration of a single oral and intravenous bolus dose. Lat. Am. J. Pharm. 29(3): 428-435, 2010.*
Merali et al. "Longitudinal Assessment of Imatinib's Effect on the Blood-Brain Barrier After Ischemia/Reperfusion Injury with Permeability MRI", Transl. Stroke Res. 6:39-49 (2015).
Rieckmann "Imatinib buys time for brain after stroke", Nature Medicine 14(7):712-713 (2008).
International Search Report corresponding to International Application No. PCT/SE2017/050183 dated May 23, 2017.
Written Opinion of the International Searching Authority corresponding to International Application No. PCT/SE2017/050183 dated May 23, 2017.
"Examination Report corresponding to European Application No. 17760399.0 dated Jul. 28, 2020".
Extended European Search Report corresponding to European Patent Application No. 17760399.0 (9 pages) (dated Dec. 4, 2019).
Ma et al. "PDGFR-alpha Inhibition Preserves Blood-Brain Barrier After Intracerebral Hemorrhage" Annals of Neurology, 70(6):920-931 (2011).

* cited by examiner

IMATINIB FOR USE IN THE TREATMENT OF STROKE

STATEMENT OF PRIORITY

This application is a 35 U.S.C. § 371 national phase application of PCT Application No. PCT/SE2017/050183 filed Feb. 27, 2017, which claims priority to Swedish Application No. 1650260-1 filed Feb. 29, 2016, the entire contents of each of which is incorporated by reference herein.

TECHNICAL FIELD

This disclosure relates generally to the field of medicine and the treatment of stroke, and in particular to a novel method and use in the treatment of stroke involving the administration of Imatinib or Nilotinib at a prescribed dose for at least 3 consecutive days.

BACKGROUND

A stroke is defined as the sudden death of brain cells in a localized area due to interrupted or inadequate blood flow. According to the European Cardiovascular Disease Statistics 2012, stroke is the second single most common cause of death in Europe: accounting for almost 1.1 million deaths each year. Over one in seven women (15%) and one in ten men (10%) die from the disease (Melanie Nichols et al., European Cardiovascular Disease Statistics, 2012 Edition, Department of Public Health, University of Oxford).

Depending on the causative factor and progression, a stroke can be designated as one of the following two main types:

Ischemic stroke, which occurs as a result of an obstruction, or clot, within a blood vessel supplying blood to the brain. This accounts for the vast majority of all stroke cases.

Hemorrhagic stroke, which occurs when a blood vessel ruptures. The reason for the rupture can be an aneurysm or an arteriovenous malformation, which can be congenital defects. The most common cause is however uncontrolled hypertension.

The following disclosure will focus on ischemic stroke, and in particular acute ischemic stroke, but is not limited thereto. The goal of all existing treatments of ischemic stroke is to quickly restore the blood flow and to prevent or at least reduce the likelihood of another stroke. Currently, the only FDA approved treatment for ischemic strokes is tissue plasminogen activator (tPA, ALTEPLASE®, ACTIVASE®). tPA works by dissolving the clot and improving blood flow to the part of the brain being deprived of blood flow. If administered early tPA may improve the chances of recovering from a stroke. tPA is however known to have serious side effects such as neurotoxicity and increased vascular permeability due to an altered blood-brain barrier function. There are indications that the balance between the positive effects of tPA and the side effects becomes less favourable to the patient when the onset of tPA therapy is delayed. The exact thresholds vary, but it is recommended in general that tPA therapy should be started as soon as possible, and preferably not later than 4-5 hours after the stroke. Sometimes an even narrower therapeutic window is recommended.

Before administering tPA or other pharmaceutical thrombolysis, it has to be determined if the patient suffers from an acute ischemic stroke of from a hemorrhagic stroke. In the case of haemorrhage, the thrombolysis would worsen the condition. The symptoms alone are usually not specific enough to make this distinction, so usually the patient is subjected to a CT scan or MRI scan to rule out any intracranial haemorrhage. Only then can thrombolytic treatment be started. Depending on the available resources and diagnostic capabilities, this may delay the starting time of thrombolytic therapy, or even make the care giver refrain from such therapy altogether as a precaution. Further, in order to be most effective, thrombolysis should be started within 3 hours from the occurrence of the stroke, preferably as early as possible.

Thrombolysis is the treatment of choice for acute stroke within 3 to 4.5 hours after symptom onset. There are trials indicating that alteplase 3-4.5 h after onset was better than placebo, and a registry study supporting this. Professional recommendations have issued in favour of these results but remain to be fully accepted. However, there are indications that late onset thrombolytic therapy may be associated with more severe side effects. As a consequence, it is possible that a patient does not receive the most appropriate therapy, either because of an uncertainty in the diagnosis (ischemic v. hemorrhagic stroke), or a delay in reaching the diagnosis (delays in obtaining a CT, or the lack of the necessary equipment), or a combination. In practice, only about 10% of the patients receive thrombolytic therapy. Other treatments include mechanical thrombectomy, i.e. the surgical removal or disintegration of the clot, and antiplatelet therapy, preventing new clots from forming. Cumulating experience shows that thrombectomy significantly increases the odds of recovery or at least reduces the neurological damage following a stroke. Unlike thrombolytic drugs, the anti-platelet agents do not have effect on clots that are already present. Aspirin is the most commonly used anti-platelet agent, and there are indications that it is effective for the early treatment of acute ischemic stroke, preferably in combination with dipyridamol.

WO 2007/124308 discloses methods and compositions for preventing or ameliorating the side effects, and for improving the treatment, or extending the treatment window, of tPA where thrombolysis is desired, by using platelet-derived growth factor (PDGF) and PDGF receptor antagonism to counter the undesirable effects of tPA. WO 2007/124308 also discloses a combination therapy in the treatment of ischemic stroke using tPA and a PDGF receptor antagonist. Imatinib mesylate is given as one example of suitable substances that inhibit the PDGF receptor.

In any case, considering the high prevalence of acute ischemic stroke, and the serious consequences such as disabilities and death, there is a need for improved treatments and new drugs.

SUMMARY

One objective is to improve the treatment of acute ischemic stroke, regardless if this involves surgical removal of a clot or clots (thrombectomy) or pharmaceutical thrombolytic treatment, such as the administration of a tissue plasminogen activator, or antiplatelet therapy, or a combination thereof.

Another objective is to widen the therapeutic window for thrombolysis, by making it possible to start thrombolytic therapy later than currently recommended.

Yet another objective is to make available new methods for the treatment of stroke, not limited to acute ischemic stroke, but also applicable for example to hemorrhagic stroke.

Further objectives, corresponding aspects of the invention, and the advantages associated with the solutions offered by the invention, will become evident to a person skilled in the art upon study of the description and examples, together with the claims appended hereto.

According to a first aspect, the present inventors disclose that Imatinib (GLEEVEC®, GLIVEC®, STI-571, a tyrosine kinase inhibitor) can be used in the treatment of acute ischemic stroke, wherein said Imatinib is administered to a patient at a dose of 650 mg/day or higher for at least 3 consecutive days, preferably for at least 4 consecutive days, and most preferably for at least 5 consecutive days.

According to an embodiment of said first aspect said Imatinib is administered to a patient at a dose of 700 mg/day or higher, preferably 750 mg/day or higher, more preferably 800 mg/day or higher.

According to yet another embodiment, freely combinable with the above, said Imatinib is administered to a patient prior to, concurrent with, or subsequent to thrombectomy (surgical removal or breakdown of a clot).

According to yet another embodiment, freely combinable with the above, said Imatinib is administered to a patient prior to, concurrent with, or subsequent to thrombolysis (pharmacological breakdown of a blood clot).

According to a preferred embodiment, freely combinable with the above, said Imatinib is administered to a patient prior to, undergoing or having undergone thrombectomy and thrombolysis.

Most preferably Imatinib is administered to a patient as soon as possible, even before it has been determined if the patient has suffered an acute ischemic stroke or a hemorrhagic stroke.

According to yet another embodiment, freely combinable with the above, said thrombolysis comprises the administration of a tissue plasminogen activator (tPA), preferably chosen from alteplase (ACTIVASE®), reteplase (RETEVASE®, RAPILYSIN®) and tenecteplase (TNKase®).

According to a preferred embodiment, freely combinable with the above embodiments, said Imatinib is administered to a patient at a starting dose of 1000 mg/day or higher on day 1, and at a dose in the interval of 650 mg/day to 1000 mg/day on the subsequent days.

While the starting dose should be higher that the subsequent dose, it is currently contemplated that Imatinib should not be given at a higher dose than 1600 mg/day as the starting dose. Further, it is contemplated that Imatinib should not be given at doses higher than 1200 mg/day on any of the consecutive days. According to yet another embodiment, freely combinable with the above, said Imatinib is administered orally.

According to an alternative embodiment, freely combinable with the above, wherein said Imatinib is administered intravenously. It is also contemplated that at least a portion of the starting dose of Imatinib is administered intravenously, whereas the subsequent, consecutive doses are administered orally.

According to a second aspect, the present inventors make available a method for the treatment of acute ischemic stroke, wherein Imatinib (GLEEVEC®, GLIVEC®, STI-571, a tyrosine kinase inhibitor) is administered to a patient at a dose of 650 mg/day or higher for at least 3 consecutive days, preferably for at least 4 consecutive days, and most preferably for at least 5 consecutive days.

According to an embodiment of said second aspect Imatinib is administered to a patient at a dose of 700 mg/day or higher, preferably 750 mg/day or higher, more preferably 800 mg/day or higher.

According to yet another embodiment, freely combinable with the above, Imatinib is administered to a patient prior to, concurrent with, or subsequent to thrombectomy. Thrombectomy is here understood as any surgical removal or breakdown of a clot, regardless of the method used.

According to yet another embodiment, freely combinable with the above, Imatinib is administered to a patient prior to, concurrent with, or subsequent to thrombolysis. Thrombolysis is here understood as the pharmacological breakdown of a blood clot, regardless of the particular drug or pharmacological treatment used.

According to a preferred embodiment, freely combinable with the above, Imatinib is administered to a patient prior to, undergoing or having undergone thrombectomy and thrombolysis.

Most preferably Imatinib is administered to a patient as soon as possible, even before it has been determined if the patient has suffered an acute ischemic stroke or a hemorrhagic stroke.

According to yet another embodiment, freely combinable with the above, wherein said thrombolysis comprises the administration of a tissue plasminogen activator (tPA) (chosen from alteplase (ACTIVASE®), reteplase (RETEVASE®, RAPILYSIN®) and tenecteplase (TNKase®).

According to a preferred embodiment, freely combinable with the above, said Imatinib is administered to a patient at a starting dose of 1000 mg/day or higher on day 1, and at a dose in the interval of 650 mg/day to about 1000 mg/day on the subsequent days. While the starting dose should be higher that the subsequent dose or doses, it is currently contemplated that Imatinib should not be given at a higher dose than 1600 mg/day as the starting dose.

Further, it is contemplated that Imatinib should not be given at doses higher than 1200 mg/day on any of the consecutive days.

According to yet another embodiment, freely combinable with the above, Imatinib is administered orally.

According to an alternative embodiment, freely combinable with the above, Imatinib is administered intravenously. It is also contemplated that the at least a portion of the starting dose of Imatinib is administered intravenously, whereas the subsequent, consecutive doses are administered orally.

The steps of any method disclosed herein do not have to be performed in the exact order disclosed, unless explicitly stated.

A particular embodiment includes a pharmaceutical composition for intravenous administration comprising Imatinib at a dose in a range of 400 to 1200, preferably 800 to 1000 mg in a suitable solution for intravenous administration, for example in 0.8-1.0% NaCl solution, such as 500 ml 0.9% NaCl solution.

The pharmaceutical composition for intravenous administration can be prepared in a hospital pharmacy, at the intensive care ward, or bedside (Point-of-care). Imatinib should be stored away from heat, moisture, and light. Preferably Imatinib is provided in lyophilized form, stored in sealed vials of dark glass, possibly in admixture with one or more suitable stabilizing agents. When preparing a composition for intravenous administration, the lyophilized Imatinib is reconstituted by the addition of sterile WFI or saline, and added to a solution for i.v. administration in a desired concentration.

A specific embodiment is thus the use of a pharmaceutical composition suitable for intravenous administration, said composition comprising Imatinib and optionally adjuvants and excipients, in the treatment of stroke.

Another embodiment is a kit of parts, comprising Imatinib, preferably in lyophilized form, and a solution suitable for reconstituting the lyophilized Imatinib, and a solution suitable for intravenous administration, and optional adjuvants and excipients. In a particular embodiment, Imatinib is supplied in doses of 400 mg and 800 mg in separate vials, and the solution suitable for intravenous administration is 0.8-1.0% NaCl solution, preferably 0.9% NaCl solution, supplied in containers, such as flexible bags with a volume of 50 ml, 100 ml, 250 ml, 500 ml or 1000 ml, preferably 500 ml.

It is currently preferred that Imatinib is administered intravenously, but as Imatinib is available in tablet form, it is contemplated that a starting dose of Imatinib is administered intravenously, during at least Day 1 of the treatment, whereas Imatinib during the remaining treatment is administered orally. Thus, yet another embodiment is a kit of parts, comprising a solution of 1000 mg Imatinib in 500 ml 0.9% NaCl, and n*400 mg Imatinib tablets, where n is an integer between 2 and 4.

Further aspects and embodiments will become apparent to a person skilled in the art upon study of the figures and the following detailed description and examples.

BRIEF DESCRIPTION OF THE DRAWINGS

The invention and embodiments thereof is now described, by way of example, with reference to the accompanying drawings, in which:

FIG. 1 illustrates the logistic characteristics of the clinical study. The first arrow from the left represents "In total, 60 patients recruited between February 2011 and November 2014". The second arrow from the left represents "All patients treated with iv thrombolysis initiated within 4.5 h: Stroke onset to start: Median 1 h 25 m Range: 0 h 35 m-4 h 25 m". The third arrow from the left represents "25 patients treated with mechanical thrombectomy, ended within 7 h 45 min: Stroke onset to end: Median 4 h 38 m Range: 2 h 25 m-7 h 45 m". The fourth arrow from the left represents "43 randomised to imatinib (17 to control): Stroke onset to first dose: Median 4 h 00 m Range: h5 m-11 h 54 min".

DETAILED DESCRIPTION

Before the present invention is described, it is to be understood that the terminology employed herein is used for the purpose of describing particular embodiments only and is not intended to be limiting, since the scope of the invention will be limited only by the appended claims and equivalents thereof.

It must be noted that, as used in this specification and appended claims, the singular forms "a", "an" and "the" also include plural referents unless the context clearly dictates otherwise.

Also, the term "about" is used to indicate a deviation of +/−2% of a given value, preferably +/−5%, and most preferably +/−10% of the given value, where applicable.

Tyrosine kinase inhibitors (TKIs) are bioactive, usually aromatic, small molecules that are currently investigated for use in the treatment of cancer, inflammatory, metabolic, proliferative and neurodegenerative diseases. Tyrosine kinase inhibitors can bind to the active site of a TK receptor thus preventing phosphorylation and by doing so inhibit, regulate or modulate signalling, often with cytostatic activity. Some potent kinase inhibitors will exhibit selectivity for a certain TK receptors, while others are less selective. For example, some compounds are potent and selective inhibitors of Vascular Endothelial Growth Factor Receptor (VEGFR) receptor kinases, but weak inhibitors of Platelet Derived Growth Factor Receptor (PDGFR) tyrosine kinases and Epidermal Growth Factor Receptor (EGFR) tyrosine kinases.

Eight TKI medications, including Imatinib and Gefitinib, have been approved by the Food and Drug Administration for use in humans as of today. One TKI, Toceranib (Palladia), was recently approved for the treatment of cancer in dogs. Erlotinib (Tarceva), which like Gefitinib, inhibits EGFR. Lapatinib (Tykerb) is a dual inhibitor of EGFR and a subclass called Human EGFR type 2. EGFR isn't the only growth factor targeted. Sunitinib (Sutent) is multi-targeted, inhibiting PDGFR and VEGF.

Other tyrosine kinase inhibitors are more specialized. Sorafenib (Nexavar) targets a complex pathway that would lead to a kinase signalling cascade. Nilotinib (Tasigna), another small-molecule tyrosine kinase inhibitor, also inhibits the fusion protein bcr-abl and is typically prescribed when a patient has shown resistance to Imatinib. Nilotinib also targets PDGF receptors. There are indications that Nilotinib is more potent than Imatinib, for example 10-30 fold more potent than Imatinib in inhibiting Bcr-Abl tyrosine kinase activity. Nilotinib is currently commercially available as 150 mg and 200 mg hard gelatine capsules. It is contemplated that the findings made in the clinical study using Imatinib, and the subsequently defined new and surprising uses of Imatinib as well as the new methods for the treatment of stroke, are also transferrable to Nilotinib with appropriate adjustment of dose.

More TKIs are currently in development, though the process is slow and more drugs end up being abandoned during clinical phases than get approved. Three TKIs are currently showing promise in clinical trials. Bosutinib targets abl and src kinases. Neratinib, like Lapatinib, inhibits EGFR and Human EGFR type 2. Vatalanib inhibits both VEGFR and PDGFR.

According to a first aspect, the present inventors disclose that Imatinib (GLEEVEC®, GLIVEC®, STI-571, a tyrosine kinase inhibitor) can be used in the treatment of acute ischemic stroke, wherein said Imatinib is administered to a patient at a dose of 650 mg/day or higher for at least 3 consecutive days, preferably for at least 4 consecutive days, and most preferably for at least 5 consecutive days. The exact dose can be adjusted by the treating physician, and adapted to the severity of the condition, the age and sex of the patient, body weight and other particulars of the patient.

According to an embodiment of said first aspect said Imatinib is administered to a patient at a dose of 700 mg/day or higher, preferably 750 mg/day or higher, more preferably 800 mg/day or higher.

According to yet another embodiment, freely combinable with the above, said Imatinib is administered to a patient prior to, concurrent with, or subsequent to thrombectomy.

The term "thrombectomy" is here used to define any surgical and/or mechanical removal or breakdown of a clot. In the United States, three classes of mechanical thrombectomy devices have been cleared by the FDA; coil retrievers, aspiration devices, and stent retrievers. Other devices and methods, currently under development, are also included in the definition of thrombectomy used herein.

According to yet another embodiment, freely combinable with the above, said Imatinib is administered to a patient prior to, concurrent with, or subsequent to thrombolysis. The term "thrombolysis" is here used to define any pharmacological breakdown of a blood clot. The currently most commonly used drug for thrombolytic therapy is tissue plasminogen activator (tPA), but there are alternative drugs that achieve the same effect. Thrombolysis may involve the injection of a thrombolytic drug through an intravenous (IV) line or through a long catheter that delivers the drug directly to the site of the blockage. The chance of surviving and recovering from acute ischemic stroke is significantly improved if the patient is administered a thrombolytic drug within 12 hours after the stroke. Ideally, thrombolytic treatment should be given within the first 30 minutes after arrival at the hospital. Most preferably Imatinib is administered to a patient as soon as possible, even before it has been determined if the patient has suffered an acute ischemic stroke or a hemorrhagic stroke.

Both thrombectomy and thrombolysis are emergency treatments, and should be given as soon as possible. For practical reasons, thrombolytic treatment is usually initiated before thrombectomy can be performed, but as stated under the heading "Summary", the steps of any method disclosed herein do not have to be performed in the exact order disclosed, unless explicitly stated.

According to a preferred embodiment, freely combinable with the above, said Imatinib is administered to a patient prior to, undergoing or having undergone thrombectomy and thrombolysis. More preferably Imatinib is administered to a patient as soon as possible, even before it has been determined if the patient has suffered an acute ischemic stroke or a hemorrhagic stroke. An advantage of this is that the administration of Imatinib as such improves the outcome for the patient, and additionally makes it possible to start thrombolysis therapy later, also outside the recommended window, in cases where there has been delays for example in the patient reaching the hospital, or delays in making a correct diagnosis, or a delay in determining that the patient has suffered from an ischemic stroke and not from a hemorrhagic stroke, for example due to delays in obtaining access to CT or MRI equipment.

According to yet another embodiment, freely combinable with the above, said thrombolysis comprises the administration of a tissue plasminogen activator (tPA), preferably chosen from alteplase (ACTIVASE®), reteplase (RETEVASE®, RAPILYSIN®) and tenecteplase (TNKase®). While the present disclosure focuses on the above mentioned tPA drugs, other drugs currently under development and pending approval can also be useful in a combination treatment.

According to a preferred embodiment, freely combinable with the above embodiments, said Imatinib is administered to a patient at a starting dose of 1000 mg/day or higher on day 1, and at a dose in the interval of 650 mg/day to 1000 mg/day on the subsequent days. While the starting dose should be higher than the subsequent dose, it is currently contemplated that Imatinib should not be given at a higher dose than 1600 mg/day as the starting dose. Further, it is contemplated that Imatinib should not be given at doses higher than 1200 mg/day on any of the consecutive days. Again, the exact dose can be adjusted by the treating physician, and adapted to the severity of the condition, the age and sex of the patient, body weight and other particulars of the patient.

According to a specific embodiment, Imatinib is formulated and administered to the patient as follows: 800 mg Imatinib is dissolved in a NaCl solution, such as 500 ml 0.9% NaCl, or other suitable i.v. solution, and administered to the patient during about 12 hours. Following this initial dose, 400 mg Imatinib in 500 ml of a suitable i.v. solution is given for the consecutive 12 hour period. This amounts to a starting dose of 1200 mg/day on Day 1, and 800 mg/day on each consecutive day.

According to yet another embodiment, freely combinable with the above, said Imatinib is administered orally. Oral administration forms include, but are not limited to tablets, capsules, caplets, suspensions, and solutions. A skilled person within the field of galenic chemistry can prepare a suitable oral administration form without undue burden.

According to an alternative embodiment, freely combinable with the above, said Imatinib is administered intravenously. Intravenous administration forms include conventional i.v. solutions, such as saline (0.9% sodium chloride in sterile water), hypotonic saline (0.45% or 0.33% sodium chloride is sterile water), hypertonic saline (3-5% sodium chloride in sterile water), dextrose in water, dextrose in saline, and electrolyte solutions, for example Ringer's solution. Imatinib is preferably administered by adding the desired dose to normal saline solution, for example 650 mg Imatinib to 500 ml saline. Imatinib can for example be given in concentrations such as 400 mg/500 ml, 500 mg/500 ml, 600 mg/500 ml, 700 mg/500 ml, and 800 mg/500 ml i.v. solution.

The treating physician may however prescribe the addition of Imatinib to another i.v. solution, depending on the condition of the patient. Further, a person skilled within the field of galenic chemistry can prepare a suitable intravenous administration form without undue burden.

It is also contemplated that at least a portion of the starting dose of Imatinib is administered intravenously, whereas the subsequent, consecutive doses are administered orally.

Based on the findings obtained for Imatinib, it is also contemplated that Nilotinib can be used in the same fashion, with appropriate adjustment of dose. Consequently, according to an additional aspect, the present inventors make available Nilotinib for use in the treatment of acute ischemic stroke, wherein said Nilotinib is administered to a patient at a dose in the range of 200 to 600 mg/day or higher for at least 3 consecutive days, preferably for at least 4 consecutive days, and most preferably for at least 5 consecutive days.

Further, said Nilotinib can be administered to a patient at a dose of 300 mg/day or higher, preferably 400 mg/day or higher, more preferably 600 mg/day or higher.

Preferably Nilotinib is administered to a patient prior to, concurrent with, or subsequent to thrombectomy, prior to, concurrent with, or subsequent to thrombolysis. Preferably Nilotinib is administered to a patient undergoing or having undergone thrombectomy and thrombolysis. Most preferably it is administered to a patient as soon as possible and already before it has been determined if the patient suffers from an ischemic stroke or a hemorrhagic stroke.

In the aspects above, relating to the use of Nilotinib, said thrombolysis comprises the administration of a tissue plasminogen activator (tPA) chosen from alteplase (ACTIVASE®), reteplase (RETEVASE®, RAPILYSIN®) and tenecteplase (TNKase®).

According to another embodiment, freely combinable with any of the above embodiments relating to Nilotinib, said Nilotinib is administered to a patient at a starting dose of 500 mg/day or higher on day 1, and at a dose in the interval of 300 mg/day to 500 mg/day on the subsequent days. Said Nilotinib is administered orally or intravenously, preferably intravenously. According to a specific embodiment, at least a portion of said starting dose is administered intravenously, and the consecutive doses are administered orally.

According to a second aspect, the present inventors make available a method for the treatment of acute ischemic stroke, wherein Imatinib (GLEEVEC®, GLIVEC®, STI-571, a tyrosine kinase inhibitor) is administered to a patient at a dose of 650 mg/day or higher for at least 3 consecutive days, preferably for at least 4 consecutive days, and most preferably for at least 5 consecutive days.

According to an embodiment of said second aspect Imatinib is administered to a patient at a dose of 700 mg/day or higher, preferably 750 mg/day or higher, more preferably 800 mg/day or higher.

According to yet another embodiment, freely combinable with the above, Imatinib is administered to a patient prior to, concurrent with, or subsequent to thrombectomy. Thrombectomy is here understood as any surgical removal or breakdown of a clot, regardless of the method used.

According to yet another embodiment, freely combinable with the above, Imatinib is administered to a patient prior to, concurrent with, or subsequent to thrombolysis. Thrombolysis is here understood as the pharmacological breakdown of a blood clot, regardless of the particular drug or pharmacological treatment used.

According to a preferred embodiment, freely combinable with the above, Imatinib is administered to a patient undergoing or having undergone thrombectomy and thrombolysis. Most preferably Imatinib is administered to a patient as soon as possible, even before it has been determined if the patient has suffered an acute ischemic stroke or a hemorrhagic stroke.

According to yet another embodiment, freely combinable with the above, wherein said thrombolysis comprises the administration of a tissue plasminogen activator (tPA) (chosen from alteplase (ACTIVASE®), reteplase (RETEVASE®, RAPILYSIN®) and tenecteplase (TNKase®).

According to a preferred embodiment, freely combinable with the above, said Imatinib is administered to a patient at a starting dose of 1000 mg/day or higher on day 1, and at a dose in the interval of 650 mg/day to about 1000 mg/day on the subsequent days. While the starting dose should be higher that the subsequent dose, it is currently contemplated that Imatinib should not be given at a higher dose than 1600 mg/day as the starting dose. Further, it is contemplated that Imatinib should not be given at doses higher than 1200 mg/day on any of the consecutive days. Again, the exact dose can be adjusted by the treating physician, and adapted to the severity of the condition, the age and sex of the patient, body weight and other particulars of the patient.

According to yet another embodiment, freely combinable with the above, Imatinib is administered orally. Oral administration forms include, but are not limited to tablets, capsules, caplets, suspensions, and solutions. A skilled person within the field of galenic chemistry can prepare a suitable oral administration form without undue burden.

According to an alternative and currently preferred embodiment, freely combinable with the above, Imatinib is administered intravenously. Intravenous administration forms include conventional i.v. solutions as exemplified above. A person skilled within the field of galenic chemistry can prepare a suitable i.v. administration form without undue burden.

It is also contemplated that at least a portion of the starting dose of Imatinib is administered intravenously, whereas the subsequent, consecutive doses are administered orally.

The steps of any method disclosed herein do not have to be performed in the exact order disclosed, unless explicitly stated.

A particular embodiment includes a pharmaceutical composition for intravenous administration comprising Imatinib at a dose of 1000 mg in 500 ml 0.9% NaCl solution. It is contemplated that, for emergency room use, ready-made i.v. solutions containing Imatinib in a suitable i.v. solution, and at a predefined dose, should be made available for immediate use. In the alternative, an i.v. solution containing Imatinib can be prepared by adding a concentrated Imatinib solution to a conventional i.v. solution, such as saline, dextrose or Ringer's.

Therefor, one embodiment is a kit of parts, comprising Imatinib, preferably in lyophilized form, and a solution suitable for reconstituting the lyophilized Imatinib, and a solution suitable for intravenous administration, and optional adjuvants and excipients. In a particular embodiment, Imatinib is supplied in doses of 400 mg and 800 mg in separate vials, and the solution suitable for intravenous administration is 0.9% NaCl solution, supplied in containers, such as flexible bags with a volume of 50 ml, 100 ml, 250 ml, 500 ml or 1000 ml, preferably 500 ml.

It is currently preferred that Imatinib is administered intravenously, but as Imatinib is available in tablet form, it is contemplated that a starting dose of Imatinib is administered intravenously, during at least Day 1 of the treatment, whereas Imatinib during the remaining treatment is administered orally. Thus, yet another embodiment is a kit of parts, comprising a solution of 1000 mg Imatinib in 500 ml 0.9% NaCl, and n*400 mg Imatinib tablets, where n is an integer between 2 and 4.

It is contemplated that, for emergency room use, different kits are made available, containing Imatinib both in the form of an i.v. solution, in different concentrations, and optionally also in an oral administration form, at the prescribed doses, and instructions for use, to allow for rapid and safe administration to a patient in need thereof.

Yet another aspect and embodiments thereof relate to a method for the treatment of acute ischemic stroke, wherein Nilotinib is administered to a patient at a dose in the range of 200 to 600 mg/day or higher for at least 3 consecutive days, preferably for at least 4 consecutive days, and most preferably for at least 5 consecutive days.

Further, in an embodiment of said method, Nilotinib is administered to a patient at a dose of 300 mg/day or higher, preferably 400 mg/day or higher, more preferably 600 mg/day or higher.

Preferably Nilotinib is administered to a patient prior to, concurrent with, or subsequent to thrombectomy. More preferably Nilotinib is administered to a patient prior to, concurrent with, or subsequent to thrombolysis. In a preferred embodiment of the method, Nilotinib is administered to the patient as soon as possible and even before it has been determined if the patient suffers from an ischemic stroke or an hemorrhagic stroke.

In an embodiment of the method, said thrombolysis comprises the administration of a tissue plasminogen activator (tPA) chosen from alteplase (ACTIVASE®), reteplase (RETEVASE®, RAPILYSIN®) and tenecteplase (TNKase®).

In yet another embodiment, freely combinable with the above embodiments, said Nilotinib is administered to a patient at a starting dose of 500 mg/day or higher on day 1, and at a dose in the interval of 300 mg/day to 500 mg/day on the subsequent days. Said Nilotinib is administered orally or intravenously, preferably intravenously. According to a specific embodiment, at least a portion of said starting dose is administered intravenously, and the consecutive doses are administered orally.

EXAMPLES

The present inventors conducted a phase II, dose escalating, safety and tolerability, regional multicentre clinical trial with randomized treatment-group assignment, open-label treatment, and blinded end-point evaluation in patients with acute ischemic stroke treated with intravenous thrombolysis.

In this study, treatment with an oral dose of Imatinib, administered orally as soon as possible on the day of arrival and for five following days, was compared to standard treatment. In a first phase of the study (n=20), a daily dose of 400 mg of Imatinib was used, followed in the next phase (n=20) by 600 mg and finally by 800 mg (n=20). Each dose increase was preceded by a safety evaluation and clearance by an independent safety committee. Randomization was 3:1, thus to create four groups of equal size (n=15), including control with a total 60 patients. All patients received intravenous thrombolysis in agreement with accepted indications, and mechanical thrombectomy in patients with large artery occlusion fulfilling local criteria for intervention.

1. Material and Methods
1.1 Patients and Participating Centers

The study was conducted at five centers in Stockholm County. Patients for which mechanical thrombectomy were considered had intravenous thrombolysis initiated at their local hospital and were then transferred to Karolinska University Hospital at Solna (KS). The patients were 18-85 years, with an acute ischemic stroke onset causing a neurological deficit of 7 to 25 points on the National Institutes of Health Stroke Scale (NIHSS). All patients were treated with intravenous thrombolysis, 0.9 mg/kg, within 4.5 hours after stroke onset in accordance with generally accepted criteria. Following informed consent, all patients were to be randomized to active treatment or control within 1 hour after termination of reperfusion treatment, whether intravenous thrombolysis alone or followed by mechanical thrombectomy. If allocated to active treatment, it had to be initiated as soon as it was practically possible after randomization.

1.2 Treatment

The first treatment occasion occurred as soon as practically possible after randomization (day 0). Treatment was given orally as a tablet of 400 mg, 600 mg or 800 mg, depending on the phase of the study. If required, tablets were crushed and given through a nasogastric tube. From day 1 to day 5, one tablet was given each morning, except for the highest dose level (800 mg) when tablets of 400 mg were given twice daily (morning and evening).

Plasma concentrations of Imatinib were examined for one patient in phase one and all patients in phase two and three at the following three time points: 1) Three hours after the first tablet administration 2) Before the morning dose day 1 3) Before the morning dose day 2. For two patients, one with 600 mg/day and one with 800 mg per day, plasma concentrations were also examined before the morning dose at day 3-5.

1.3 Outcome Measures
1.3.1 Primary Outcome

The primary outcome of this study was any serious or non-serious adverse event. A serious adverse event is defined as any untoward medical occurrence that results in death, is life threatening, requires inpatient hospitalization or prolongation of existing hospitalization, results in persistent or significant disability/incapacity or is a congenital anomaly/birth defect. A non-serious adverse event is defined as any other unfavourable an unintended sign (including, for example, an abnormal laboratory finding), symptom, or to disease temporally associated with the use of a medicinal product, whether or not considered related to the medicinal product. These measures included mortality and any untoward deviation of laboratory values, as a part of the safety evaluation.

1.3.2 Secondary Outcome

Occurrence and severity of hemorrhagic transformation, intracerebral hemorrhage and cerebral edema on post-treatment computer tomography (CT) or magnetic resonance imaging (MR) were among secondary outcomes. Others were neurological outcome at 2 hours, 24 hours and 7 days after initiation of intravenous thrombolysis, functional outcome at 3 months and infarct volume at 7 days. Infarct volume evaluation will be addressed in a following publication.

1.4 Clinical and Radiological Assessment

Clinical assessments, including determination of the NIHSS score were performed before intravenous thrombolysis and start of study treatment (baseline), 2 hours (day 0), day 1 and then daily until day 7. A final NIHSS score was included in the 3 months follow up examination. Assessment of any adverse event was done daily from day 0 to day 7, and finally at 3 months. CT scan was performed at baseline, 24 hours (accepted interval 22-36 hours) and, optionally, at 7 days, MRI at 24 h (accepted interval as for CT) and at 7 days. Definitions of hemorrhagic transformations, parenchymatous hemorrhages and edema are described in an earlier publication $R_1$ and also listed in Table 1. At three months functional status was evaluated using the modified Rankin Scale (mRS) score. The three months follow up examinations were performed blindly at a different hospital than the one responsible for the acute treatment.

TABLE 1

Definitions of hemorrhagic transformations, parenchymatous hemorrhages and cerebral edema

| Definitions of hemorrhagic transformations | |
|---|---|
| HI1: | Hemorrhagic infarct type 1, small petechiae along the margins of the infarct |
| HI2: | Hemorrhagic infarct type 2, more confluent petechiae within the infarct area but without space-occupying effect |
| PH1: | Parenchymatous Hemorrhage type 1, blood clot(s) not exceeding 30% of the infarct area with some mild space-occupying effect |
| PH2: | Parenchymatous Haemorrhage type 2, blood clots exceeding 30% of the infarct area with significant space occupying effect |
| PHr1: | Remote Parenchymatous Hemorrhage type 1, small or medium sized blood clots located remote from the actual infarct; a mild space occupying effect could be present |
| PHr2: | Remote Parenchymatous Hemorrhage type 2, large confluent dense blood clots in an area remote from the actual infarct; significant space occupying effect may be present |
| Definitions of edema | |
| CED 1: | Cerebral edema, type 1, focal brain swelling up to one third of the hemisphere |
| CED 2: | Cerebral edema, type 2, focal brain swelling greater than one third of the hemisphere |
| CED 3: | Cerebral edema, type 3, brain swelling with midline shift |

1.5 Statistical Analysis

To analyze whether Imatinib had any effect on NIHSS, the dose of Imatinib was treated both as categorical and as continuous. When looking at separate time points, linear regression with robust standard errors was used, while adjusting for thrombectomy. When looking at the mean effect over the entire time course, we used a linear mixed model with random intercept and adjustment for thrombectomy, using robust standard errors and allowing the residuals to have an autoregressive 1 (AR1) correlation within individuals. The choice of using AR1 correlation was made by comparing the Akaike Information Criterion to a model without AR1 correlation. Due to some missing NIHSS values, multiple imputationR2 was used. The association between treatment groups and functional independence was analyzed using odds ratios. The statistical software Stata v.13 was used.

2. Results 2.1 Characteristics of the Patients

Figure 1:
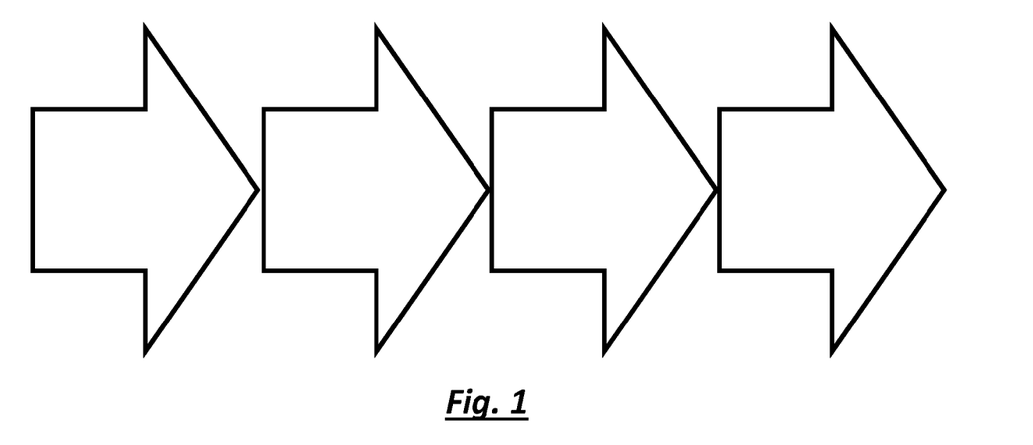

In total, 60 patients were recruited between February 2011 and November 2014, 20 patients per each dose level. Within the first dose level, 15 patients were randomized to 400 mg daily (low dose) and 5 to control. The second dose level included 14 patients allocated to treatment with 600 mg daily (medium dose) and 6 to control. In the final dose level, 14 patients were randomized to 800 mg daily (high dose) and 6 to control. Baseline characteristics are provided in Table 2 and logistic characteristics in FIG. 1.

TABLE 2

Demographic and baseline data as per ITT

|  | Control | Low | Medium | High |  |
|---|---|---|---|---|---|
| Number of pts | 17 | 15 | 14 | 14 |  |
| Age(median) | 70 | 76 | 73 | 72 | NS |
| % Male | 65 | 53 | 79 | 43 | NS |
| % Hypertension | 76 | 73 | 64 | 50 | NS |
| % Atrial fibrillation | 29 | 33 | 43 | 36 | NS |
| % Diabetes | 18 | 20 | 7 | 7 | NS |
| % Hyperlipidemia | 35 | 20 | 29 | 36 | NS |
| % Smoker (current) | 18 | 7 | 29 | 0 | NS |
| % Smoker (previous) | 35 | 40 | 50 | 29 | NS |
| % Previous stroke (>3 M) | 12 | 7 | 0 | 7 | NS |
| % Previous TIA | 12 | 13 | 7 | 0 | NS |
| Baseline NIHSS | 13 | 12 | 11 | 13 | NS |
| IVT % | 100 | 100 | 100 | 100 | NS |
| IAT % | 0 | 7 | 0 | 0 | NS |
| MT % | 29 | 47 | 21 | 71 | NS |
| Stenting % | 6 | 13 | 0 | 7 | NS |
| Aspirin % | 31 | 47 | 36 | 21 | NS |
| Warfarin % | 6 | 0 | 8 | 7 | NS |
| Oral antidiabetic % | 7 | 7 | 0 | 7 | NS |
| Insulin % | 6 | 0 | 8 | 0 | NS |
| Statin % | 50 | 20 | 21 | 21 | NS |

All patients were included in the safety analysis in accordance with intention to treat. Other analyses were performed in agreement with their actual treatment. Thus three patients in the first dose level were removed from per protocol analysis since they received some, but incomplete, doses. One patient intended for 400 mg per day did not receive any treatment and were analyzed as control. One patient intended for 600 mg did instead receive 400 mg per day and was included in the corresponding dose group. Consequently, for the per protocol analysis, the control group included 18 patients, low dose group 12 patients, medium dose group 13 patients and high dose group 14 patients.

2.2 Plasma Concentrations of Imatinib

Figure 2:
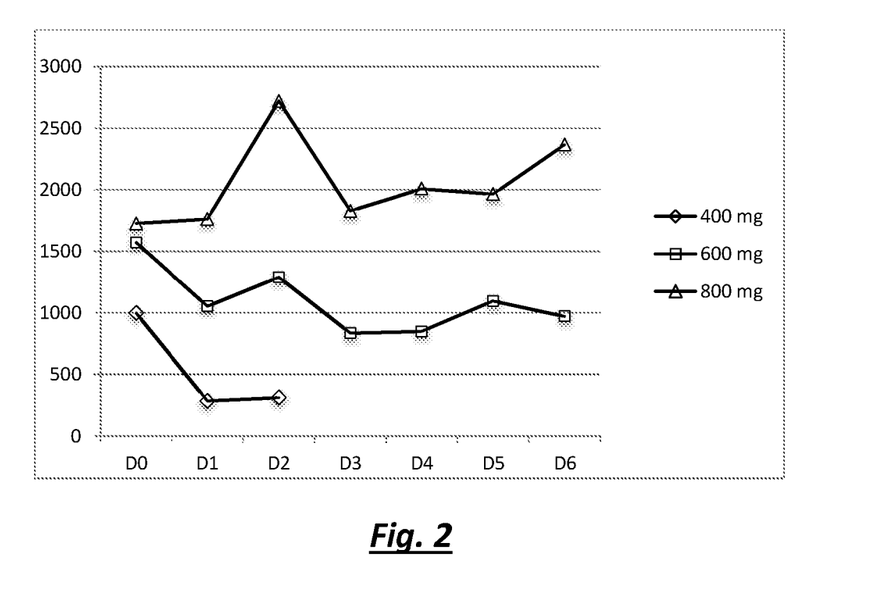
FIG. 2 is a graph showing the plasma concentrations (ng/ml) of Imatinib as a function of time (Day 0 to Day 6) for three different doses, 400, 600 and 800 mg. D0=3 h after first dose; D1-D5=before the morning dose day 1-5; D6=on the morning of day 6. For each 600 mg and 800 mg D0-D2, N=14; for each 400 mg and for each 600 mg and 800 mg D3-D6, N=1.
Figure 3:
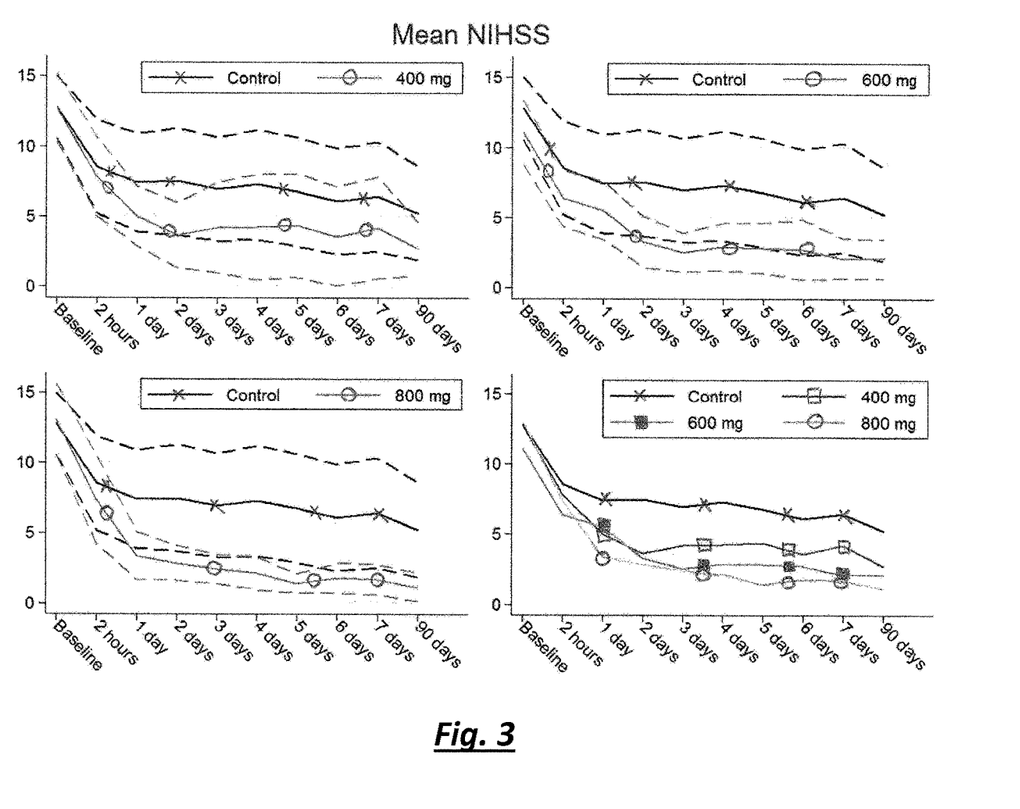
FIG. 3 shows the results as the mean score according to the Institutes of Health Stroke Scale (NIHSS)
Figure 4:
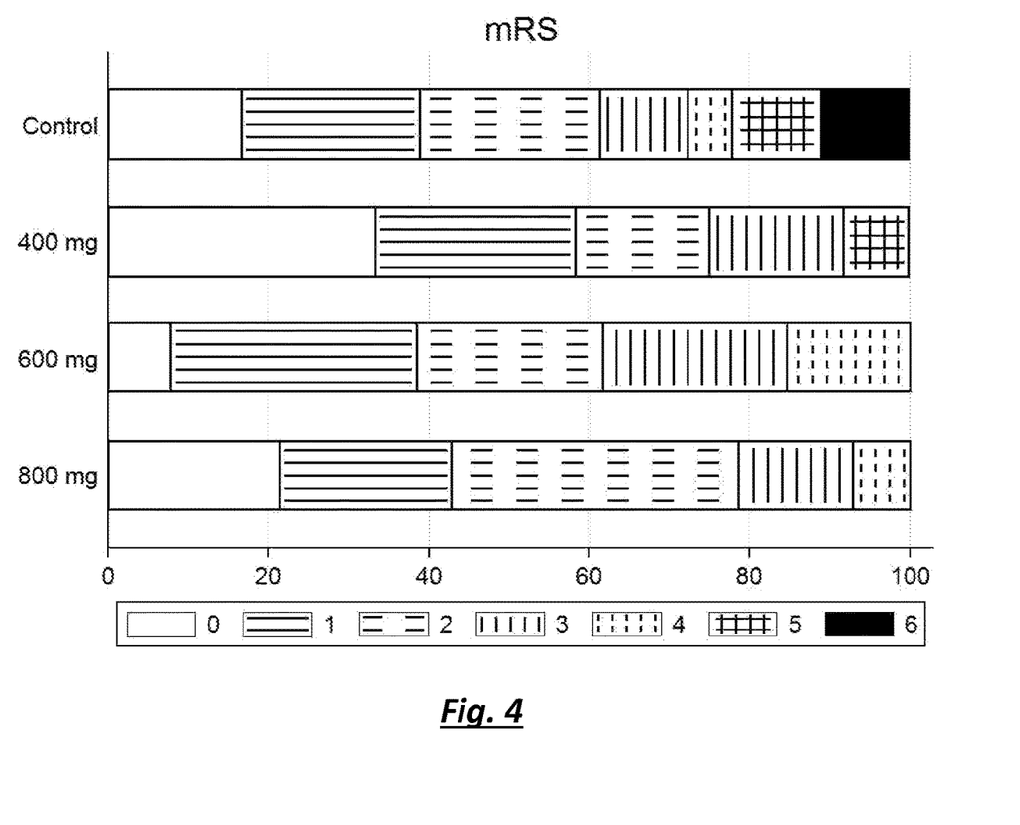
FIG. 4 shows the results according to a modified Rankin scale. A score of 0-2 indicates functional independence.

The mean plasma concentration of Imatinib during the period from Day 0-Day 6 was 530 ng/ml (95% CI 74-987) for 400 mg daily, 1094 ng/ml (797-1391) for 600 mg daily and 2054 ng/ml (1642-2465) for 800 mg daily (FIG F2). Within three hours of the first dose the plasma concentrations were 996 ng/ml for 400 mg, 1572 ng/ml for 600 mg and 1727 ng/ml for 800 mg.

2.3 Safety Analysis—Mortality

Three patients died during the study period. One patient, who was allocated to the low dose group, but did not receive active treatment, died because of an intracerebral hemorrhage. One control patient died because of an infection. A third patient, who received two doses of medium dose Imatinib, died because of a recurrent ischemic stroke.

2.4 Safety Analysis—Adverse Events

Four serious adverse events were reported, which resulted in death for the three patients reported above and clinical deterioration for one. One patient in the control group deteriorated because of fever and infection. The patient also had a growing femoral hematoma at the site of the femoral artery puncture. There were no serious adverse events in the high dose group.

In total, 118 non-serious adverse events were reported in 41 patients (Table 3), 25 of the events were in the control group, 19 in the low dose group, 44 with medium dose and 30 with high dose. The number of reported events per patient varied between 1 and 7.

TABLE 3

Adverse events

| Adverse | Control | Low | Medium | High | Total |
|---|---|---|---|---|---|
| Number of pts | 17 | 15 | 14 | 14 | 60 |
| Fever, infection | 4 (6) | 4 (7) | 4 (5) | 3 (3) | 15 (21) |
| Itching, skin | 2 (2) | 3 (3) | 0 (0) | 6 (6) | 11 (11) |
| Cerebral | 3 (3) | 0 (0) | 9 (10) | 1 (1) | 13 (14) |
| Arrhythmia, | 3 (3) | 1 (1) | 4 (5) | 2 (2) | 10 (11) |
| Nausea, | 1 (2) | 1 (2) | 2 (6) | 4 (4) | 8 (14) |
| Fall | 1 (1) | 0 (0) | 3 (4) | 1 (1) | 5 (6) |
| Dyspnea | 2 (2) | 0 (0) | 1 (1) | 1 (1) | 4 (4) |
| Systemic | 1 (1) | 0 (0) | 1 (1) | 2 (3) | 4 (5) |
| Fainting | 0 (0) | 0 (0) | 0 (0) | 2 (2) | 2 (2) |
| Other | 6 (6) | 5 (6) | 10 (11) | 5 (5) | 26 (28) |

As can be seen in the table, the most common adverse events were fever and infection (21), cerebral bleeding (15), nausea and vomiting (12), arrhythmia including tachycardia and bradycardia (10), and itching and skin reactions (10). Itching/skin reactions and nausea/vomiting were slightly more common with the higher doses. Most of the cerebral bleedings were found in the medium dose group.

Most of the non-serious adverse events were mild (74), 42 of these were considered unrelated or unlikely related, 25 possibly or probably related and 7 were not classified. Of all mild events, 73 recovered and 1 was not classified. For 29 patients, adverse events were reported moderately severe, with 16 unrelated or unlikely related and 13 possibly or probably related. Most of these recovered (21), 4 recovered with sequels and for one patient in the control group, the symptoms were ongoing. Three patients were not classified. Severe non-serious adverse events occurred in 3 patients, 2 in the control group and one, judged unlikely related, in the medium dose group. The latter recovered, although one control patient recovered with sequels and one experienced ongoing symptoms. In 14 patients, severity was not classified; of these 9 were unrelated or unlikely related and 1 possibly related. Four recovered, 4 control patients and six others were not classified regarding outcome of the event.

2.5 Hemorrhagic Transformations

There were totally 22 hemorrhagic transformations (3 HI1, 16 HI2) in the study, 6 each in the control and low dose groups, 7 with medium dose and 3 with high dose. Three parenchymatous hemorrhages were reported. One PH1 type occurred in the control group, one with high dose and one PH2 with medium dose.

In addition, five remote parenchymatous hemorrhages of the milder grade (PHr1) were reported, one each in the low and medium groups and 3 in the high dose group.

For patients with initiation of treatment with Imatinib within 5 hours after stroke onset there were no hemorrhages reported of 5 treated in the high dose group, while this occurred in 5 of to treated in medium dose and in 4 of 8 treated in the low dose group.

For patients who had their reperfusion treatment (intravenous thrombolysis only or in combination with thrombectomy) completed within 4.5 hours, no hemorrhages were reported in the high dose group of 7 treated, while within the same time frame 6 hemorrhages of 11 treated were found in medium dose, 5 of 9 were found with low dose and 6 of 16 in the control group.

2.6 Cerebral Edema

There were in overall 33 cerebral edema (28 CED 1; 3 CED-2 and 2 CED-3) in the study, 9 in the control group, 6 in low dose, 8 in medium dose and to in high dose. The mildest form, CED 1, was seen in 7 patients in control, 4 in low dose, 7 in medium dose and in all to in the high dose. Two moderately severe edema (CED-2) was found in the low dose group and 1 with medium dose. Two severe edema (CED-3) were in control.

For patients with initiation of treatment with Imatinib within 5 hours after stroke onset, 2 of 5 patients in the high dose group had CED 1 at follow up, while 5 of to patients with medium dose and 4 of 8 patients with low dose had CED 1 or 2.

For patients who had their reperfusion treatment (intravenous thrombolysis only or in combination with thrombectomy) completed within 4.5 hours, 4 of 7 patients in the high dose group had CED 1, 6 of 11 with medium dose, 4 of nine with low dose and 8 of 16 in the control group had CED 1 or 2; The control group also included 1 patient with CED 3.

The invention has mainly been described above with reference to a few embodiments. However, as is readily appreciated by a person skilled in the art, other embodiments than the ones disclosed above are equally possible within the scope of the invention, as defined by the appended patent claims.

2.7 Neurological Outcome

Treatment with Imatinib significantly improved neurological outcome. The improvement was 0.6 points on the National Institutes of Health Stroke Scale (NIHSS) per 100 mg Imatinib after adjustment for the effect of thrombectomy. The mean lowering (improvement) of the NIHSS score was, after adjustment for thrombectomy, 2 points for low dose ($-2.30$; 95% CI $-6.30-1.70$a; $p<0.259$), 3 points for medium dose ($-3.05$; 95% CI $-6.75$ $-0.64$; $p<0.106$) and 5 points for high dose ($-4.94$; $-8.78$, $-1.11$; $p<0.012$). For all individual time points except baseline and 2 hours, there was a statistically significant lowering of the adjusted mean NIHSS score for patients treated with high dose Imatinib compared to control for day 1 by 5 points ($-5.28$; $-95\%$ CI $-9.60$, $-0.96$; $p<0.018$), for 7 days by 6 points ($-5.68$; 95% CI $-10.38$ $-0.98$; $p<0.019$) and for 3 months by 5 points ($-4.81$; 95% CI $-10.39$, $-0.98$; $p<0.019$).

2.8 Functional Outcome

Functional outcome was measured on the modified Rankin Score (mRS). Functional independence (mRS 0-2) was seen in 61% in the control group, 72% of all Imatinib treated patients, and in 79% of the high dose treated patients. For high dose, this was a 17% absolute increase of the proportion of functional independence (OR 2.33; 95% CI 0.48-11.44; $p<0.296$). Two patients in the control group scored severe disability (5 points on mRS) and 2 patients died (6 points), while this did not occur in any of the Imatinib treated patients.

The invention claimed is:

1. A method for the treatment of stroke, wherein Imatinib is administered to a patient at a dose of 650 mg/day or higher for at least 5 consecutive days.

2. The method according to claim 1, wherein Imatinib is administered to a patient at a dose of 700 mg/day or higher.

3. The method according to claim 1, wherein Imatinib is administered to a patient prior to, concurrent with, or subsequent to thrombectomy.

4. The method according to claim 1, wherein Imatinib is administered to a patient prior to, concurrent with, or subsequent to thrombolysis.

5. The method according to claim 3, wherein Imatinib is administered to a patient undergoing or having undergone thrombectomy and thrombolysis.

6. The method according to claim 4, wherein said thrombolysis comprises the administration of a tissue plasminogen activator (tPA) chosen from alteplase, reteplase and tenecteplase.

7. The method of claim 1, wherein Imatinib is administered to a patient before it has been determined if the patient suffers from an acute ischemic stroke or a hemorrhagic stroke.

8. The method according to claim 1, wherein said Imatinib is administered to a patient at a starting dose of 1000 mg/day or higher on day 1, and at a dose in the interval of 650 mg/day to about 1000 mg/day on the subsequent days.

9. The method according to claim 8, wherein Imatinib is administered orally or intravenously.

10. The method according to claim 1, wherein a starting dose of Imatinib is administered intravenously during at least day 1 of the treatment, whereas Imatinib during the remaining treatment is administered orally.

11. The method according to claim 8, wherein at least a portion of said starting dose is administered intravenously, and the consecutive doses are administered orally.

12. The method according to claim 2, wherein the dose is 750 mg/day or higher.

13. The method according to claim 2, wherein the dose is 800 mg/day or higher.

14. The method according to claim 4, wherein Imatinib is administered to a patient undergoing or having undergone thrombectomy and thrombolysis.

15. The method according to claim 7, wherein said Imatinib is administered to a patient at a starting dose of 1000 mg/day or higher on day 1, and at a dose in the interval of 650 mg/day to about 1000 rig/day on the subsequent days.

16. The method according to claim 15, wherein Imatinib is administered orally or intravenously.

17. The method according to claim 7, wherein a starting dose of Imatinib is administered intravenously during at least Day 1 of the treatment, whereas Imatinib during the remaining treatment is administered orally.

18. The method according to claim 15, wherein at least a portion of said starting dose is administered intravenously, and the consecutive doses are administered orally.

* * * * *

UNITED STATES PATENT AND TRADEMARK OFFICE
CERTIFICATE OF CORRECTION

PATENT NO. : 10,953,010 B2  
APPLICATION NO. : 16/080529  
DATED : March 23, 2021  
INVENTOR(S) : Eriksson et al.

Page 1 of 1

It is certified that error appears in the above-identified patent and that said Letters Patent is hereby corrected as shown below:

On the Title Page

Item [30]: delete "1650260" and insert -- 1650260-1 --

In the Specification

Column 14, Line 67: delete "HI12" and insert -- HI2 --

Column 15, Line 11: delete "5 of to" and insert -- 5 of 10 --

Column 15, Line 25: delete "all to in" and insert -- all 10 in --

Column 15, Line 53: delete "-1.70a" and insert -- -1.70 --

In the Claims

Column 16, Line 55, Claim 15: delete "1000 rig/day" and insert -- 1000 mg/day --

Signed and Sealed this  
Twenty-second Day of June, 2021

Drew Hirshfeld  
*Performing the Functions and Duties of the*  
*Under Secretary of Commerce for Intellectual Property and*  
*Director of the United States Patent and Trademark Office*